(12) United States Patent
Hansson et al.

(10) Patent No.: US 11,529,178 B2
(45) Date of Patent: Dec. 20, 2022

(54) TARGETING DEVICE FOR FIXATION OF BONE FRAGMENTS AT A BONE FRACTURE

(71) Applicant: SWEMAC INNOVATION AB, Linköping (SE)

(72) Inventors: Henrik Hansson, Vreta Kloster (SE); Lars Öster, Lidköping (SE)

(73) Assignee: SWEMAC INNOVATION AB, Linkoping (SE)

( * ) Notice: Subject to any disclaimer, the term of this patent is extended or adjusted under 35 U.S.C. 154(b) by 0 days.

(21) Appl. No.: 16/772,903

(22) PCT Filed: Dec. 20, 2017

(86) PCT No.: PCT/EP2017/083945
§ 371 (c)(1),
(2) Date: Jun. 15, 2020

(87) PCT Pub. No.: WO2019/120528
PCT Pub. Date: Jun. 27, 2019

(65) Prior Publication Data
US 2020/0305939 A1    Oct. 1, 2020

(51) Int. Cl.
*A61B 17/86* (2006.01)
*A61B 17/80* (2006.01)
*A61B 17/17* (2006.01)

(52) U.S. Cl.
CPC ........ *A61B 17/808* (2013.01); *A61B 17/1728* (2013.01); *A61B 17/8625* (2013.01)

(58) Field of Classification Search
CPC .............. A61B 17/808; A61B 17/1728; A61B 17/3469; A61B 17/3496; A61B 17/1721; A61B 1/32; A61F 2002/4628
See application file for complete search history.

(56) References Cited

U.S. PATENT DOCUMENTS 8,172,886 B2 * 5/2012 Castaneda .......... A61B 17/1728
606/291
8,808,300 B2 * 8/2014 Leyden .............. A61B 17/1728
606/96

(Continued)

FOREIGN PATENT DOCUMENTS

DE   102015116090    3/2017
JP    2015091420 A    5/2015
(Continued)

OTHER PUBLICATIONS

Japanese Office Action for corresponding Japanese Application Serial No. 2020-534372, dated Nov. 1, 2021, pp. 1-10.
(Continued)

*Primary Examiner* — Kevin T Truong
*Assistant Examiner* — Tracy L Kamikawa
(74) *Attorney, Agent, or Firm* — Tarolli, Sundheim, Covell & Tummino LLP

(57) ABSTRACT

A targeting device (100) for use in fixation of bone fragments at a bone fracture. The targeting device comprises an elongated body portion (110) comprising a first body end (111), an opposed second body end (112), and body through holes (113*a*, 113*b*, 113*c*) extending from the first body end to the second body end for guiding a respective fixation means (303; 303*a*, 303*b*, 303*c*) through the body portion. In its second body end the body portion is configured with a snap-fitting means (114) configured to removably attach a fixation plate (150) to the body portion such that fixation through holes (151) of the plate are located in line with a respective body through hole and, when in use, to provide a surface of the plate to abut a surface of an outer bone fragment for subsequent fixation of the plate to the fragment. The targeting device comprises further a bracket (120).

20 Claims, 15 Drawing Sheets

(56) References Cited

U.S. PATENT DOCUMENTS

| | | | |
|---|---|---|---|
| 9,427,265 B2* | 8/2016 | Paul | A61B 17/7074 |
| 2005/0015093 A1 | 1/2005 | Suh et al. | |
| 2007/0093848 A1 | 4/2007 | Harris et al. | |
| 2009/0012571 A1 | 1/2009 | Perrow et al. | |
| 2009/0312801 A1* | 12/2009 | Lemoine | A61B 17/8061 |
| | | | 606/301 |
| 2013/0012945 A1* | 1/2013 | Chreene | A61B 17/1728 |
| | | | 606/80 |
| 2014/0371799 A1* | 12/2014 | Sixto | A61B 17/8061 |
| | | | 606/281 |
| 2015/0201975 A1 | 7/2015 | Paul | |
| 2015/0201976 A1 | 7/2015 | Humphreys et al. | |
| 2017/0245903 A1 | 8/2017 | Wolf et al. | |
| 2018/0177510 A1* | 6/2018 | Whitaker | A61B 17/8057 |
| 2019/0090925 A1* | 3/2019 | Detweiler | A61B 17/1789 |

FOREIGN PATENT DOCUMENTS

| | | | |
|---|---|---|---|
| JP | 2017501826 A | 1/2017 | |
| JP | 2020534372 A | 11/2020 | |

OTHER PUBLICATIONS

Japanese Office Action for corresponding Japanese Application Serial No. 2020-534372, dated Jun. 13, 2022, pp. 1-2.

\* cited by examiner

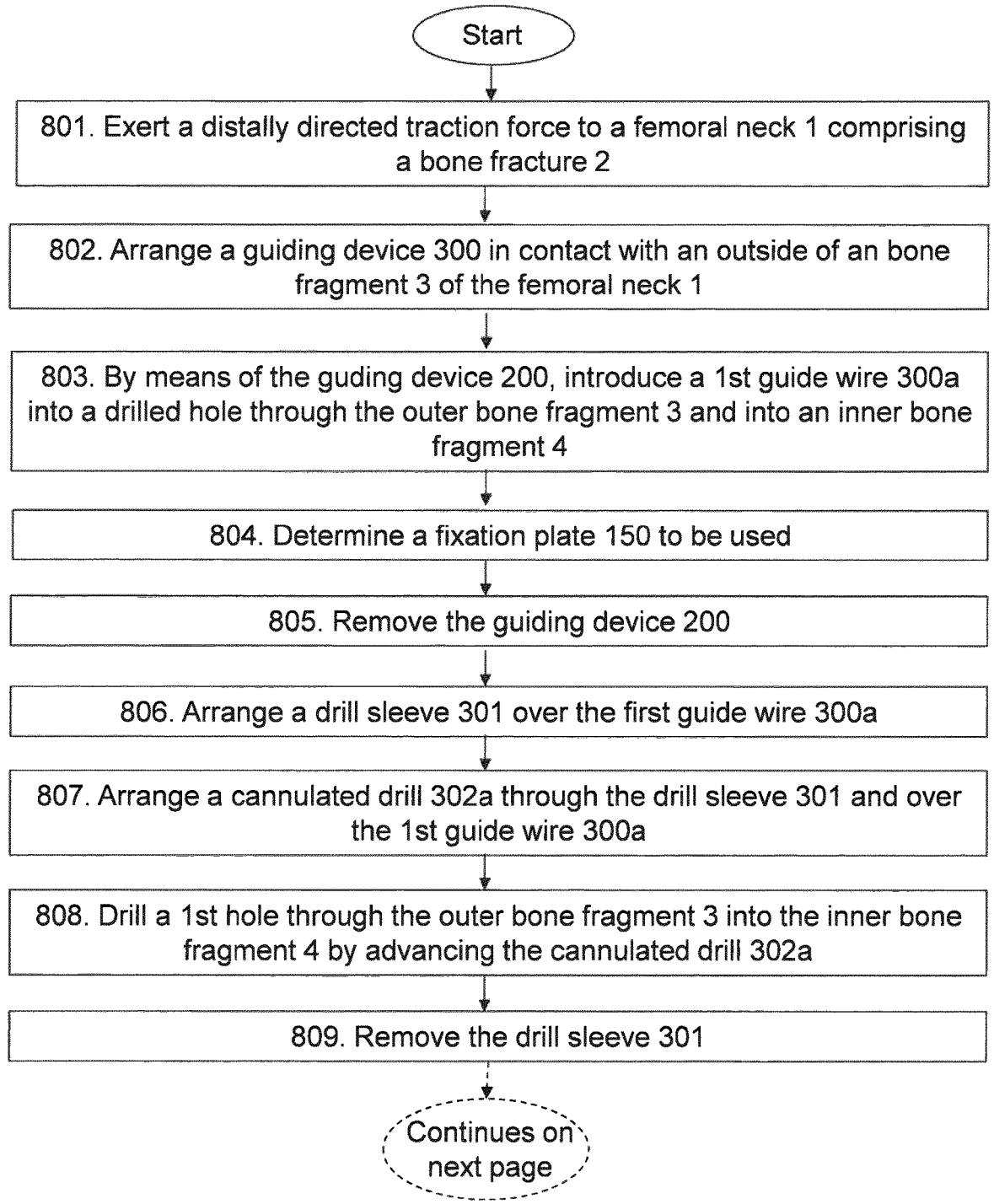
Figure 8, to be continued

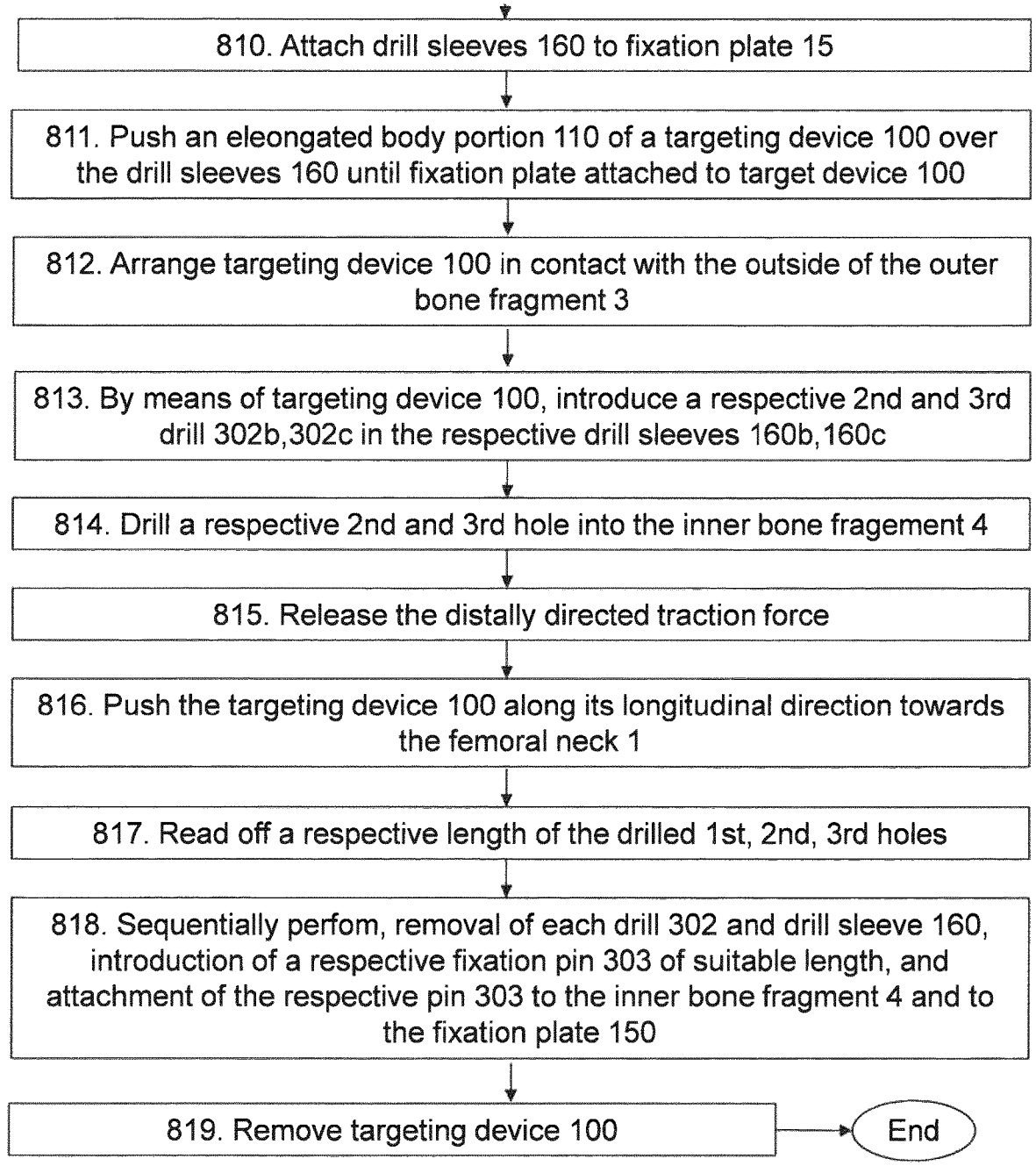
Figure 8, continued

TARGETING DEVICE FOR FIXATION OF BONE FRAGMENTS AT A BONE FRACTURE

RELATED APPLICATION

This application corresponds to PCT/EP2017/083945, filed Dec. 20, 2017.

TECHNICAL FIELD

Embodiments herein relate generally to a targeting device and a method. In particular they relate to fixation of bone fragments at a bone fracture.

BACKGROUND

After a bone fracture such as a femur neck fracture, the bone fragments at the fracture need to be fixated in order for the femur neck fracture to heal. The fixation is currently done by using a fixation plate and suitable fixation means, such as bone nails or bone screws, to fixate the fixation plate to the bone fragments.

In prior art, the fixation plate is securely attached to a targeting device by means of a plate screw, and when the fixation plate has been attached at the bone fragments by means of the fixation means, the fixation plate needs to be detached from the targeting device. This is done by releasing the plate screw using a screw driver.

SUMMARY

An object of embodiments herein is to provide an improved targeting device.

According to one aspect of embodiments herein, the object is achieved by a targeting device for use in fixation of bone fragments at a bone fracture.

The targeting device comprises an elongated body portion comprising a first body end and an opposed second body end, wherein the elongated body portion comprises a number of body through holes extending from the first body end to the second body end for guiding a respective fixation means through the body portion, and wherein the body portion in its second body end is configured with a snap-fitting means configured to removably attach a fixation plate to the body portion such that fixation through holes of the fixation plate are located in line with a respective body through hole and, when in use, to provide a surface of the fixation plate to abut a surface of an outer bone fragment for subsequent fixation of the fixation plate to the outer bone fragment by means of the fixation means.

Further, the targeting device comprises a bracket arranged at the first body end.

According to another aspect of embodiments herein, the object is achieved by a method for fixation of bone fragments at a bone fracture using a targeting device.

The method comprises exerting a distally directed traction force to a femoral neck comprising a bone fracture and arranging a guiding device in contact with an outside of an outer bone fragment of the femoral neck.

By means of the guiding device, a first guide wire is introduced into a hole drilled through the outer bone fragment and into an inner bone fragment of the femoral neck.

Further, the method comprises determining a fixation plate to be used and removing the guiding device from being in contact with the outer bone fragment.

A drill sleeve is threaded over the first guide wire arranged through the outer bone fragment and into the inner bone fragment.

Furthermore, the method comprises arranging a cannulated drill through the drill sleeve and over the first guide wire and drilling a first hole through the outer bone fragment into the inner bone fragment by advancing the cannulated drill through the outer bone fragment into the inner bone fragment.

Yet further the method comprises removing the drill sleeve and attaching first, second and third drill sleeves to the fixation plate, and pushing an elongated body portion of the targeting device over the first, second and third drill sleeves until the fixation plate is attached to a second end of the targeting device by means of a snap-fitting means.

The method comprises arranging the targeting device in contact with the outside of the outer bone fragment of the femoral neck by arranging the first drill sleeve over the cannulated drill and the first guide wire.

By means of the targeting device, a respective second and third drill is introduced in the second and third drill sleeve, respectively.

Further, by means of the second and third drills, a respective second and third drill hole is drilled through the outer bone fragment into the inner bone fragment.

The method comprises further releasing the distally directed traction force exerted to the femoral neck, pushing the targeting device along its longitudinal direction towards the femoral neck, and reading off a respective length of the drilled first, second and third holes at respective outer ends of the respective drill sleeves.

Furthermore, the method comprises sequentially performing removal of the respective first, second and third drills and the respective first, second and third drill sleeves from the targeting device; introduction of a respective first, second and third fixation means having a respective selected length through the respective first, second and third body through hole of the elongated body portion into the respective first, second and third drill hole; and attachment of the respective first, second and third fixation means to the inner bone fragment and to the fixation plate.

Yet further the method comprises removing the targeting device from being in contact with the outer bone fragment of the femoral neck.

Since the targeting device is configured to releasably retain the fixation plate by means of the snap-fitting means, the operation of the targeting device is simplified. This results in an improved targeting device.

Thus, an advantage with embodiments herein is that the targeting device is easier to use, e.g. to handle during surgery, requiring a lesser number of operation steps for fixating and releasing the fixation plate as compared to the prior art targeting devices.

Another advantage with embodiments herein is that the targeting device is configured to function as a retractor during surgery.

Yet another advantage with embodiments herein is that the targeting device is configured to function as a parallel guide for both cannulated and solid drill technique.

Yet another advantage with embodiments herein is that the targeting device is configured to function as a guide for insertion of the fixation means.

Yet another advantage with embodiments herein is that the targeting device is configured to function as a fixation plate pusher.

Yet another advantage with embodiments herein is that the targeting device is configured to minimize tension during surgery since many steps in the surgical technique is done through the fixation plate.

BRIEF DESCRIPTION OF DRAWINGS

Examples of embodiments herein are described in more detail with reference to attached drawings in which:

FIG. 8 is a flowchart depicting embodiments of a method for fixation of bone fragments at a bone fracture using a targeting device.

DETAILED DESCRIPTION

Figure 1:
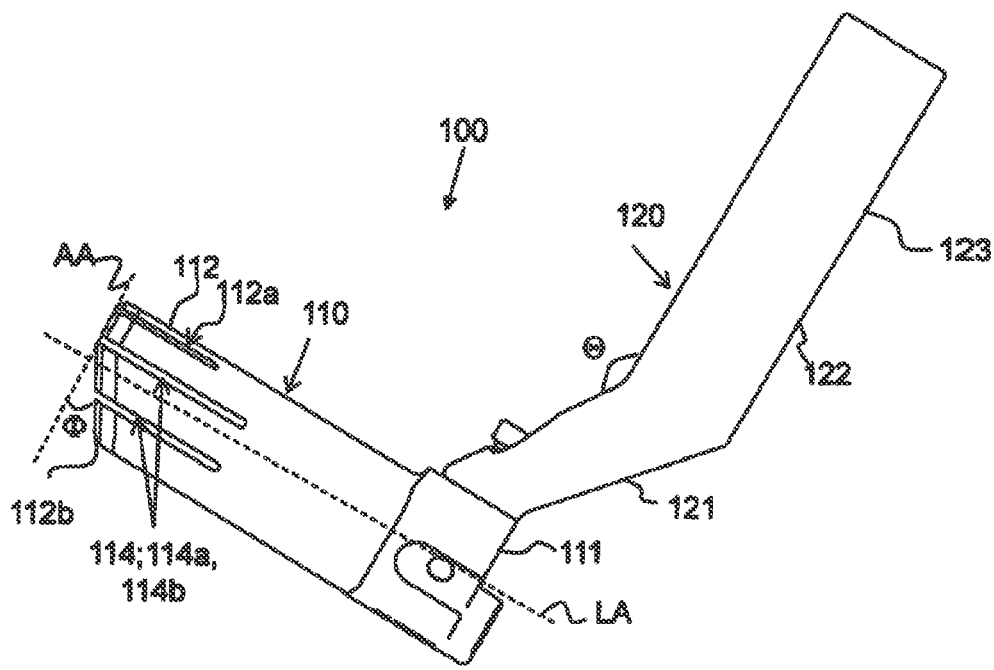
FIG. 1 schematically illustrates a side view of an embodiment of a targeting device.
Figure 2:
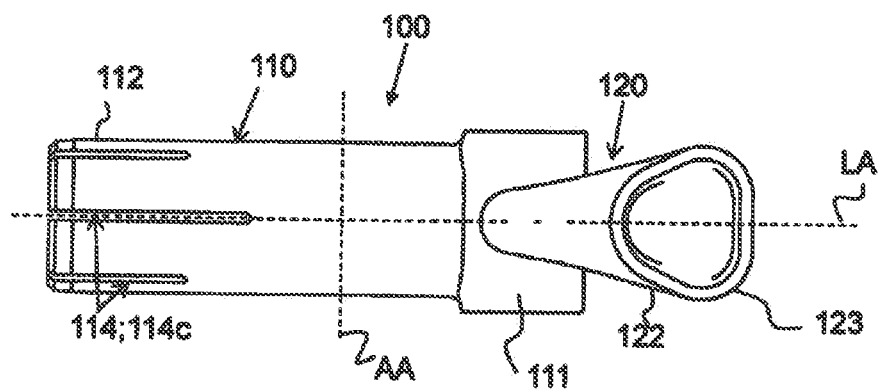
FIG. 2 schematically illustrates a top view of an embodiment of a targeting device.
Figure 3:
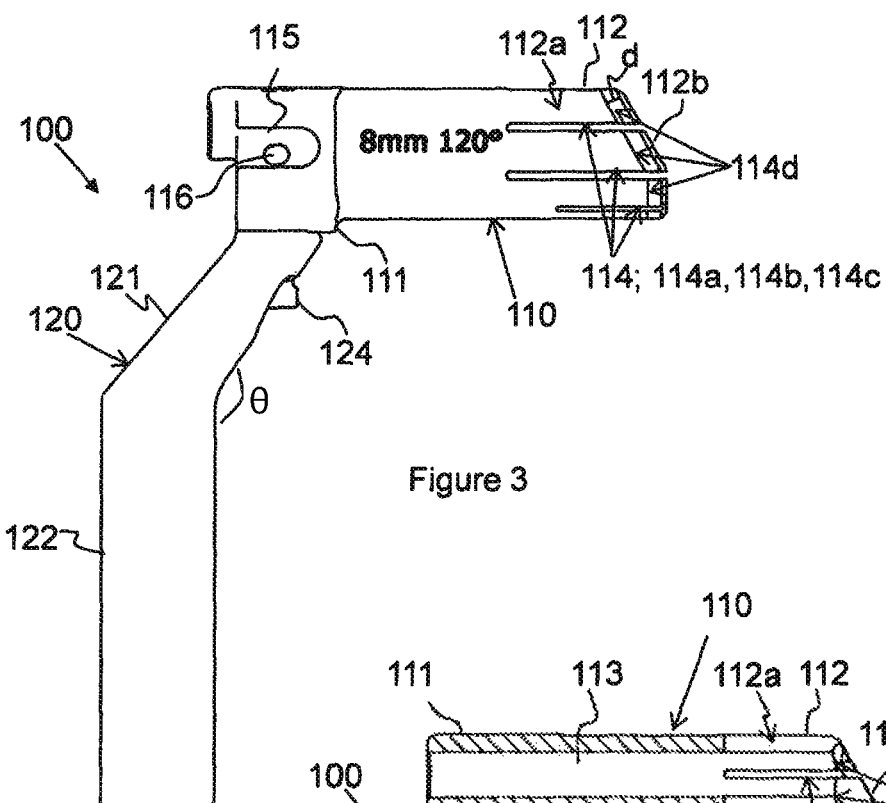
FIG. 3 schematically illustrates a side view of an embodiment of a targeting device.
Figure 4:
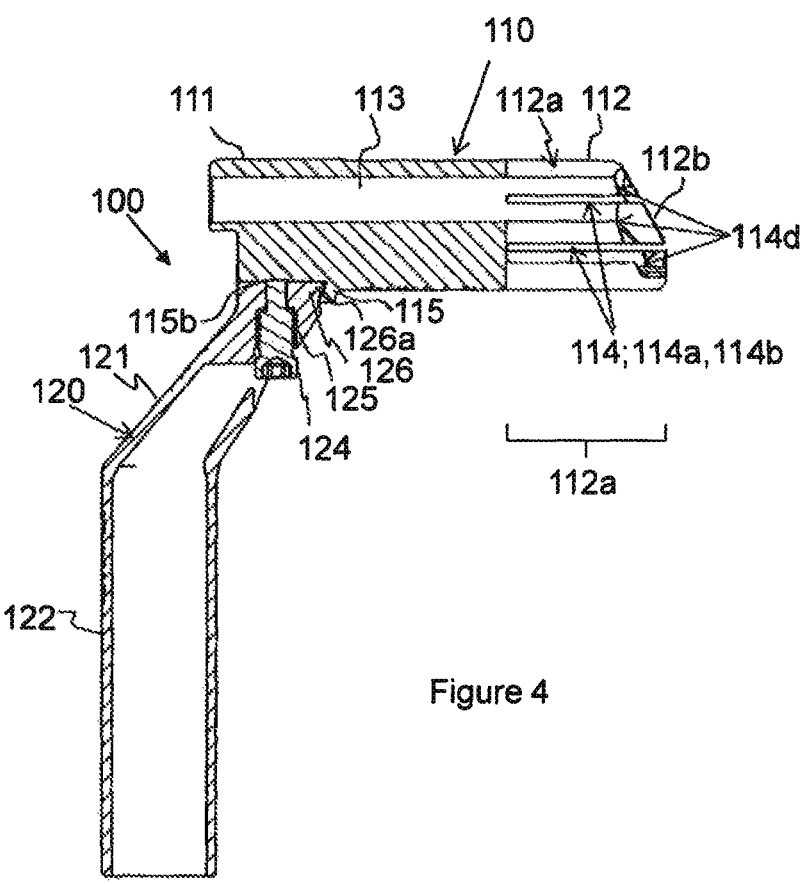
FIG. 4 schematically illustrates a cross sectional side view of an embodiment of a targeting device according to FIG. 3.
Figure 5:
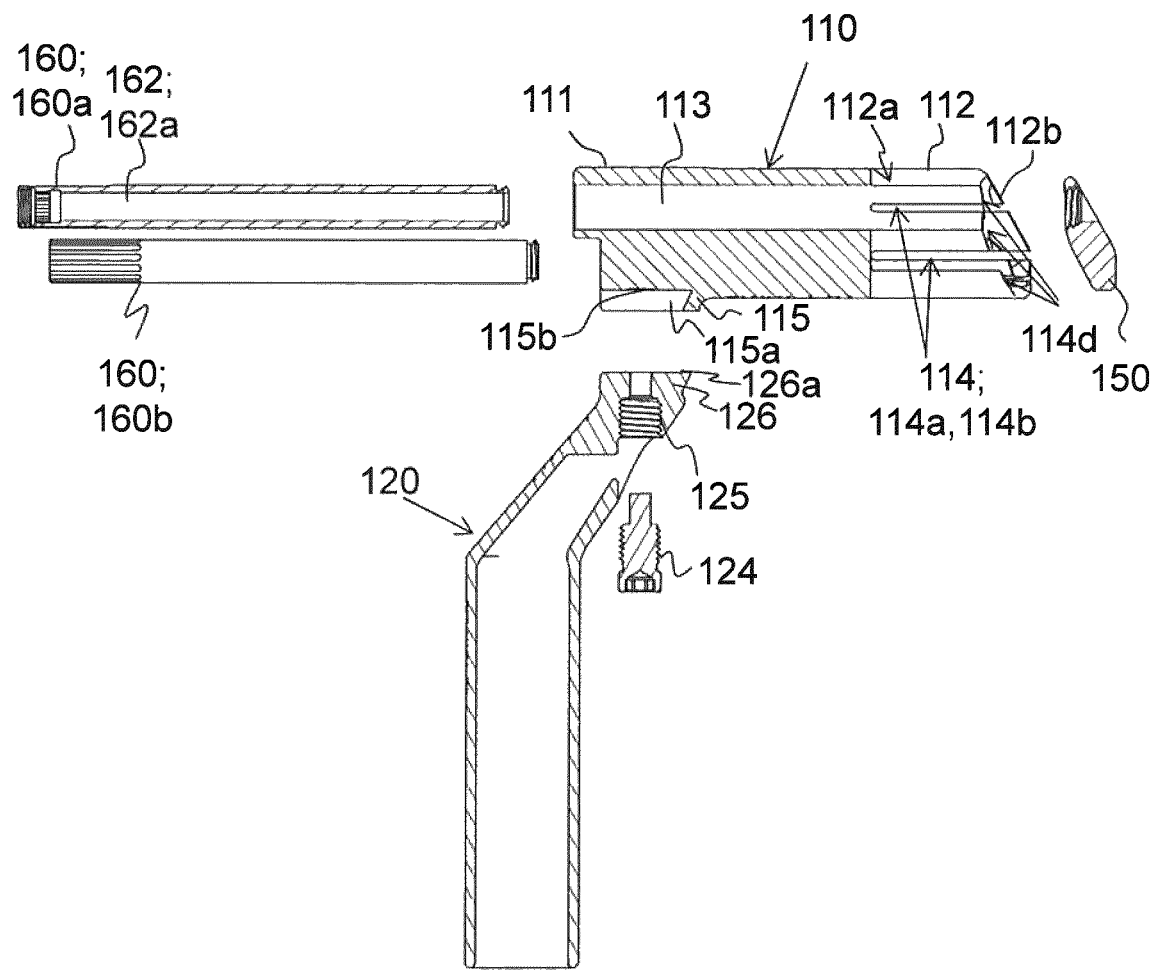
FIG. 5 schematically illustrates an exploded side view of an embodiment of a targeting device according to FIG. 3.

Below, embodiments herein will be illustrated in more detail by a number of exemplary embodiments. It should be noted that these embodiments are not mutually exclusive. Components from one embodiment may be tacitly assumed to be present in another embodiment and it will be obvious to a person skilled in the art how those components may be used in the other exemplary embodiments. In the figures, the same reference numerals are used for the same or similar components.

As schematically illustrated in for example FIGS. 1-6 and 9F-9R embodiments herein relate to a targeting device 100 for use in fixation of bone fragments 3, 4 at a bone fracture 2. For example, the bone fragments 3,4 may be an outer bone fragment 3 and an inner bone fragment 4 at a femoral neck 1.

The targeting device 100 comprises an elongated body portion 110 comprising a first body end 111 and an opposed second body end 112. The first and second body ends 111,112 are diametrically opposed body ends. The elongated body portion 110 comprises along its longitudinal direction a number of body through holes 113; 113a, 113b, 113c extending from the first body end 111 to the second body end 112 for guiding a respective fixation means 303; 303a,303b, 303c through the body portion 110.

The elongated body portion 110 may be manufactured of or comprise a plastic material such as PolyEther Ether Ketone (PEEK).

Sometimes in this disclosure the first through hole 113a is referred to as an inferior or a distal through hole and the second and third through holes 113b, 113c are referred to as superior or proximal through holes. The second and third through holes 113b, 113c may sometimes in this disclosure also be referred to as an anterior and a posterior proximal through hole, respectively.

In some embodiments, the number of through holes 113; 113a,113b,113c are configured to encompass a respective mating drill sleeve 160; 160a,160b,160c. Thus, the number of through holes 113 are configured to guide the respective mating drill sleeve 160 through the targeting device 100.

Further, the number of through holes 113a, 113b, 113c may be configured to guide a respective fixation means 303; 303a, 303b, 303c through the body portion 110 into a respective fixation through hole 151 of a fixation plate 150. The fixation means 303 is configured to fixate the fixation plate 150 to the bone fragments 3,4.

The fixation means 303 may be a bone nail or a bone screw.

The fixation means 303 may in a front end thereof comprise a hook (not shown) or a similar means configured to hook into the inner bone fragment 4. Further, the fixation means 303 may in a rear end comprise outer threads configured fit in mating inner threads of the through hole 151 of the fixation plate 150.

In some of the exemplifying figures described herein, three through holes 113a, 113b, 113c, three drill sleeves 160; 160a, 160b, 160c, and three fixation means 303; 303a,303b, 303c are shown but it should be understood that the number of through holes 113, mating drill sleeves 160 and fixation means 303 may be different, e.g. it may be lesser than or more than three.

The body portion 110 is configured with a snap-fitting means 114 in its second body end 112. The snap-fitting means 114 is configured to removably attach the fixation plate 150 to the body portion 110 such that fixation through holes 151 of the fixation plate 150 are located in line with a respective body through hole 113a,133b,113c. Thus, by means of the snap-fitting means 114 according to embodiments disclosed herein there is no need to attach the fixation plate 150 to the targeting device 100 by means of a screw or the like. Thereby, simplifying the operation of the targeting device 100 as compared to prior art targeting devices. In use, the snap-fitting means 114 is configured to provide a surface of the fixation plate 150 to abut a surface of an outer bone fragment 3 for subsequent fixation of the fixation plate 150 to the outer bone fragment 3 by means of the fixation means 303, 303a, 303b, 303c. Thereby, the fixation plate 150 will fit flush to the surface of the outer bone fragment 3.

In some embodiments, the snap-fitting means 114 is configured to release the fixation plate 150 from the body portion 110 when the snap-fitting means 114 is exposed to a force exerted in the longitudinal direction of the body portion 110 from within the body portion 110 towards the second body end 112. Thus, by means of the snap-fitting means 114 according to embodiments disclosed herein the fixation plate 150 is easy to release from the targeting device 100 as compared to prior art targeting devices wherein a screw has to be released in order to release the fixation plate.

In some embodiments, the snap-fitting means 114 comprises one or more slits 114; 114a, 114b, 114c, distributed around an envelope surface 112a of the second body end 112, wherein each one of the one or more slits 114; 114a, 114b, 114c is configured to extend in a longitudinal direction that is approximately parallel with the longitudinal direction of the body portion 110, and wherein the one or more slits 114; 114a, 114b, 114c are configured to enable the second body end 112 to removably attach the fixation plate 150 to the body portion 110 by flexing outwards and clamping around the fixation plate 150. This may be the case when the fixation plate 150 has a circumference that is larger than the circumference of the second body end 112 in an unflexed position but smaller than the circumference of the second body end 112 in a maximal flexed position.

It should be understood that the three slits 114a, 114b, 114c of the snap-fitting means 114 are only given as an example and that the snap-fitting means 114 may comprise another number of slits or another number of means providing the snap-fitting function.

On the inside of the snap-fitting means 114, e.g. at an inner surface if the snap-fitting means 114, the snap-fitting means 114 is provided with an inwardly protruding rim 114d. The protruding rim 114d is arranged at an inner circumference of the snap-fitting means 114 and at a distanced from the opening of the second body end 112. The distanced corresponds to the thickness of the fixation plate 150. The protruding rim 114d is configured to act as a stop for the fixation plate 150 in order to stop the fixation plate 150 from being pushed past the protruding rum 114d when it is pushed into the second body end 112. Since the distance d corresponds to the thickness of the fixation plate 150, the fixation plate 150 with fit flush to the opening end of the second body end 112.

The second body end 112 may be provided with an end section, e.g. a chamfered end section 112b, arranged in a plane angled an angle Φ in relation to an axial plane of the body portion 110. The axial plane extends parallel with an axial axis AA and perpendicular to a longitudinal axis LA, cf. FIG. 1. In such embodiments, and when the targeting device 100 is in use, a surface of the chamfered end section 112b is configured to abut a surface of the outer bone fragment 3. The angle Φ is in some embodiments selected such that it enables the chamfered end section 112b to fit flush with the surface of the outer bone fragment 3.

Further, the fixation plate 150 may be configured to fit flush with the chamfered end section 112b. Thus, in some embodiments, the snap-fitting means 114 and the fixation plate 150 are arranged such that the fixation plate 150 is angled to fit flush with the chamfered end section 112b when attached to the targeting device 100 by means of the snap-fitting means 114, e.g. cf. FIGS. 9F and 9G. Thereby the fixation plate 150 will fit flush to the surface of the outer bone fragment 3 and better carry load acting on the bone fragments.

Further, the targeting device 100 comprises a bracket 120 arranged at the first body end 111. In some embodiments, the bracket 120 comprises a first bracket portion 121 and a second bracket portion 122. The first and second bracket portions 121,122 may be arranged at an angle θ relative to each other. The angle θ may be selected to provide a desired working position for the surgeon when using the targeting device 100. The bracket 120 may be or may comprise a handle means 123 such as a handle bar. Further, the bracket 120 may be manufactured of or comprise a metal.

In some embodiments, the targeting device 100, e.g. the first body end 111 of the targeting device 100, comprises a first joint portion 115, and the bracket 120 comprises a mating second joint portion 126. In such embodiments, the first joint portion 115 and the mating second joint portion 126 are configured to removably attach the body portion 110 and the bracket 120 to each other.

It should be understood that the targeting device 100 may comprise several first joint portions 115 arranged around an envelope surface of the targeting device 100. Thus, the bracket 120 may be removably attached to the targeting device 100 at several positions at the envelop surface of the targeting device 100 be.

The first joint portion 115 may comprise a slot 115a configured to retain a protruding rim 126a of the mating second joint portion 126 when the protruding rim 126a is inserted into the slot 115a by means of a force applied to the bracket 120 in a direction from the first body end 111 towards the second body end 112. Further, the slot 115a is configured to release the protruding rim 126a from the slot 115a when a force is applied to the bracket 120 in a direction from the second body end 112 towards the first body end 111.

In some embodiments, the targeting device 100 comprises a fastening means, e.g. a removable fastening means 124, configured to securely attach the bracket 120 at the first body end 111. Further, the body portion 110 may comprise a recess 115b arranged at the slot 115a and extending in direction perpendicular to the longitudinal direction of the body port 110. Furthermore, the bracket 120 may comprise a bracket through hole 125 extending through at least a part of the bracket 120. In such embodiments, the removable fastening means 124 may be securely arranged at the bracket 120 and extending through the bracket through hole 125 and into the recess 115b of the body portion 110.

The removable fastening means 124 may be a screw comprising external threads 124a at at least a part thereof and the bracket through hole 125 may comprise mating internal threads 125a formed into at least a part thereof.

Figure 6:
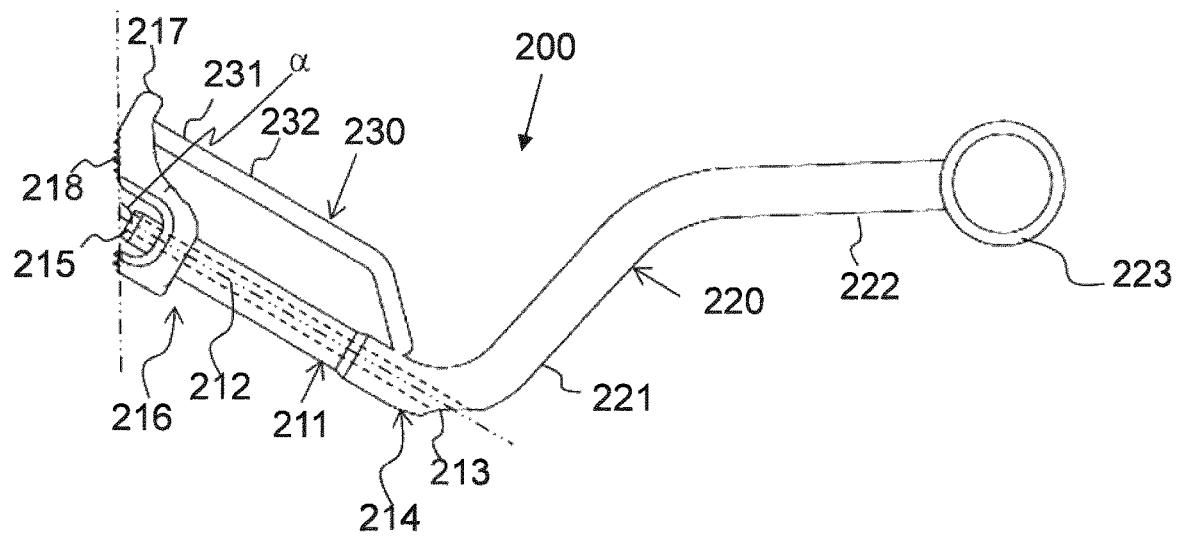
FIG. 6 schematically illustrates a side view of an embodiment of a guiding device.
Figure 7:
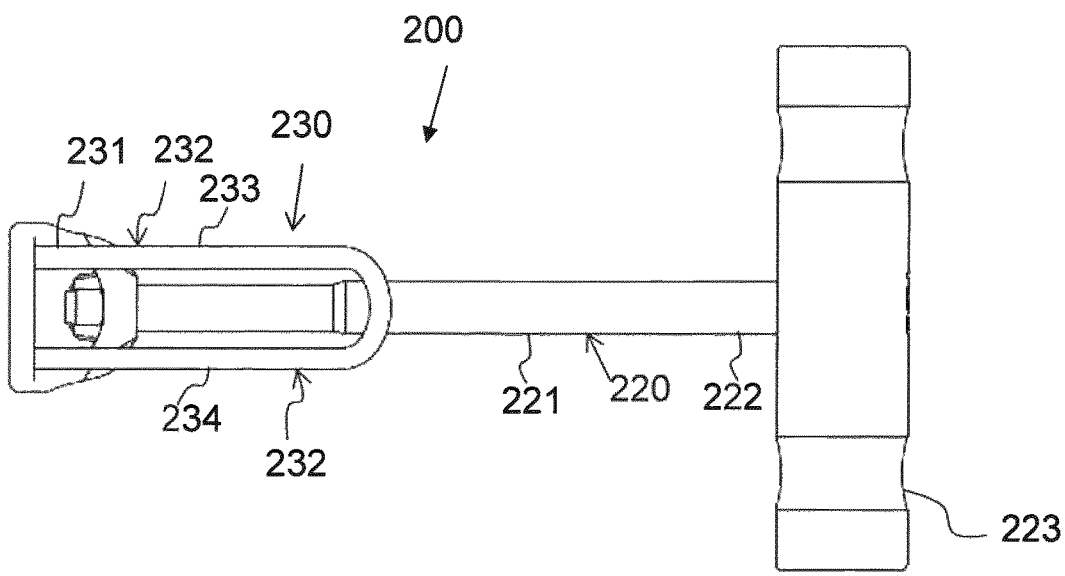
FIG. 7 schematically illustrates a top view of an embodiment of a guiding device.

FIGS. 6 and 7 schematically illustrate embodiments of a guiding device 200. The guiding device 200 is configured to ensure a desired angle α between the fixation plate 150 and the fixation means 303. The desired angle α may for example be in the range of 120 to 130 degrees, e.g. 125 degrees. The guiding device 200 is sometimes referred to as an angle guide. The guiding device 200 comprises an elongated guide portion 211 comprising, in its longitudinal direction, a longitudinal through hole 212 configured to guide a guide wire through the guide portion 211 from an inlet opening 213 in a first end 214 of the guide portion 211 to an outlet opening 215 in a second end 216 of the guide portion 212.

A handle portion 220 may be arranged at the first end 214 of the guide portion 211 and arranged angled relative to the guide portion 211. The handle portion 220 may be elongated and it may comprise a first handle section 221 and a second handle section 222. The first and second handle sections 221, 222 may be arranged angled relative to each other. Further, the second handle section 222 may comprise or may be provided with a grip 223.

The guide portion 211 may in the second end 216 comprise an abutting portion 217 having an abutting surface 218 configured to abut a surface of the outer bone fragment 3 when in use. The abutting surface 218 may be ribbed, e.g. may have a pattern of peaks, to provide a grip at the surface of the outer bone fragment 3 during use. Thanks to the abutting surface 218 the guide portion 211 will not slide along the outer bone fragment 3 during use.

An aiming means 230 may be arranged at the guide portion 211. The aiming means 230 is configured to indicate a position of a guide wire, e.g. a proximal guide wire, when in use.

A first end 231 of the aiming means 230 may be arranged at the abutting portion 217 and the aiming means 230 may be configured with an elongated first portion 232 spaced apart from the guide portion 211 and arranged in parallel with the guide portion 211. Further, the aiming means 230 may in the elongated first portion 232 comprise two spaced apart and parallel threadlike parts 233, 234, which two threadlike 233, 234 parts may be configured to indicate a respective position of a respective guide wire when in use.

It should be understood that the size and choice of material of the constituent items of devices, such as the targeting device 100 and the guiding device 200, disclosed herein may vary as necessary and desired.

Figure 9A:
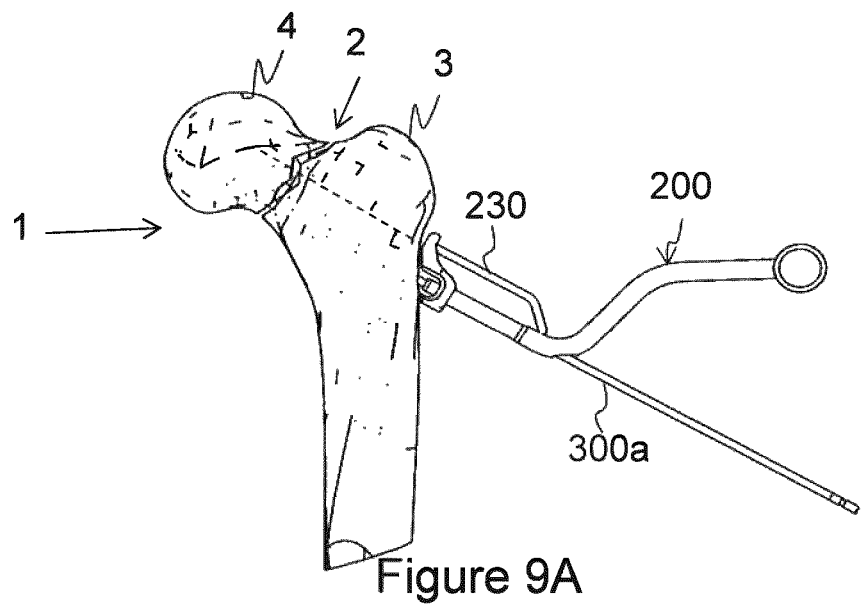
FIGS. 9A-9T schematically illustrate how devices described herein are arranged in relation to a femur neck when performing embodiments of the method for fixation of bone fragments at a bone fracture using a targeting device.
Figure 9B:
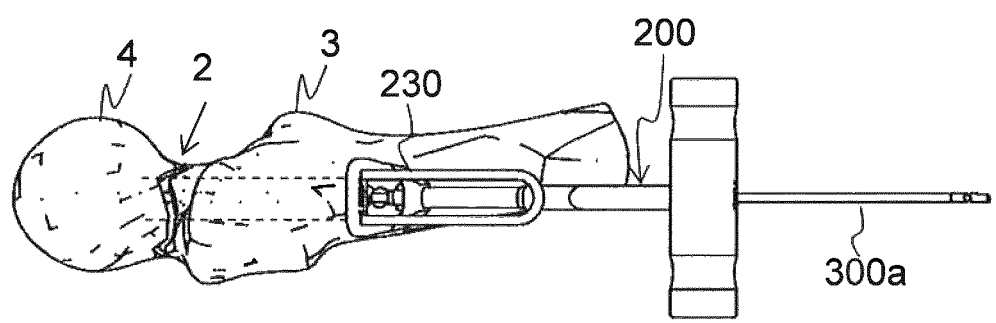
Figure 9C:
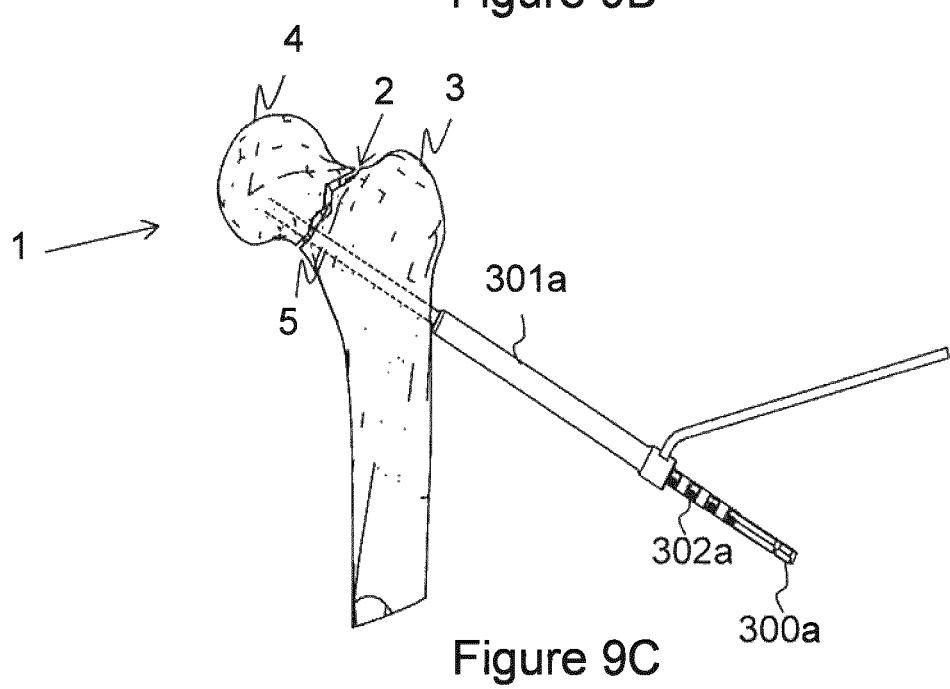
Figure 9D:
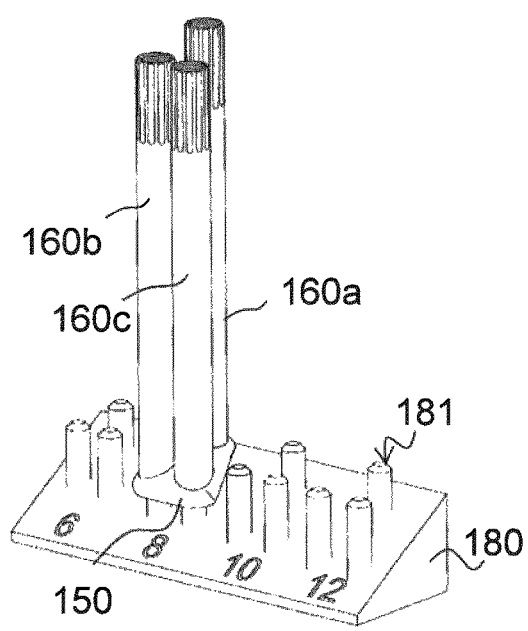
Figure 9E:
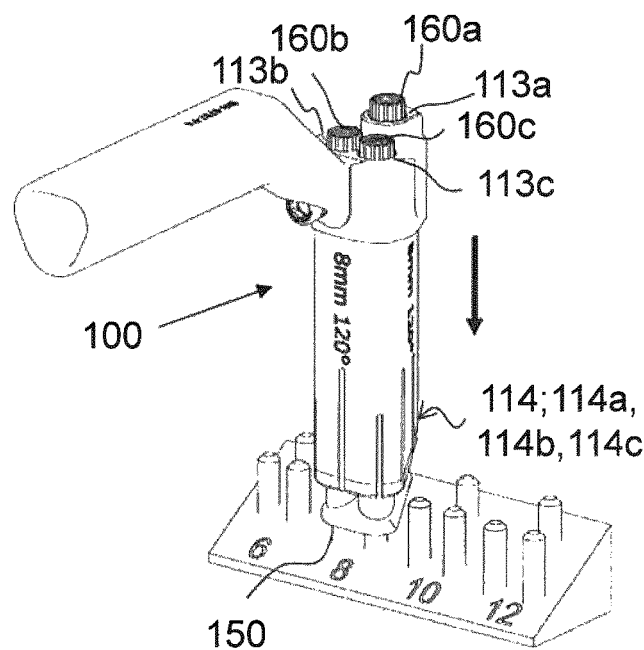
Figure 9F:
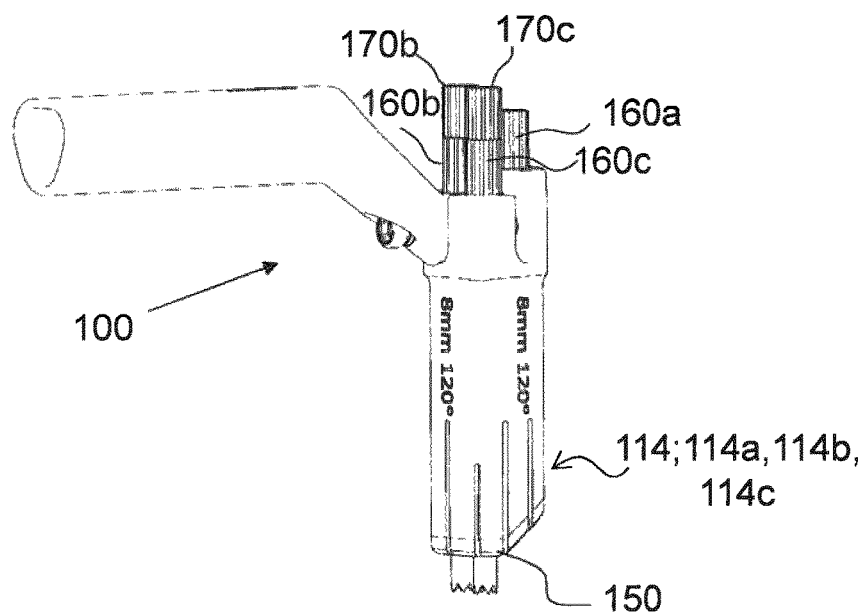
Figure 9G:
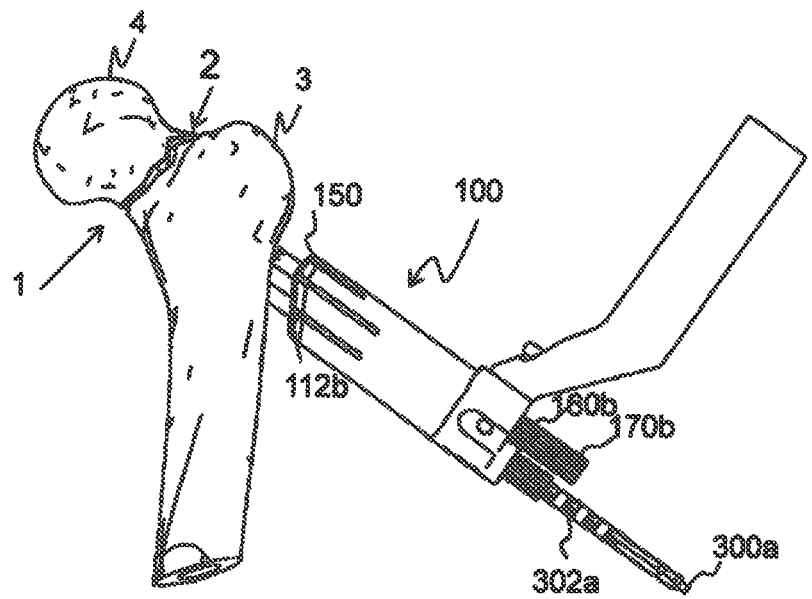
Figure 9H:
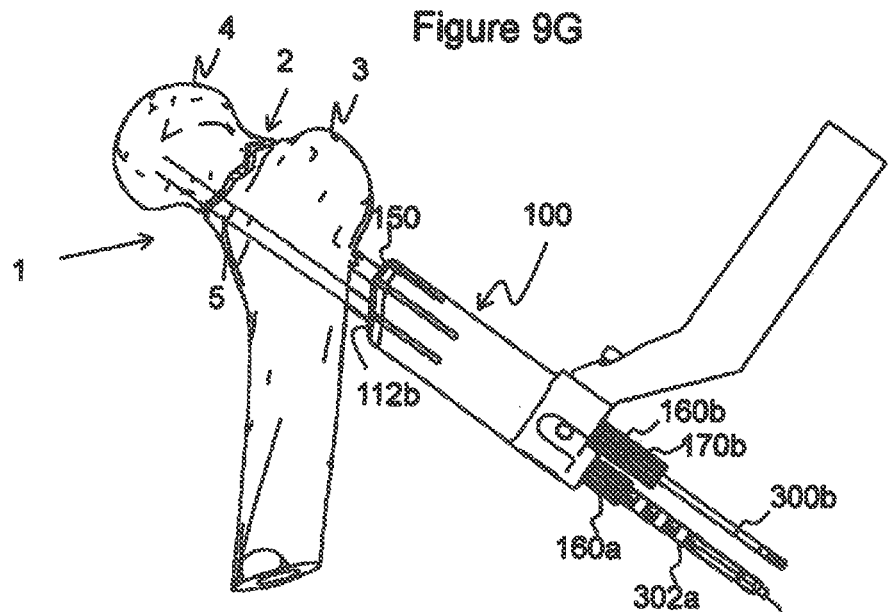
Figure 9I:
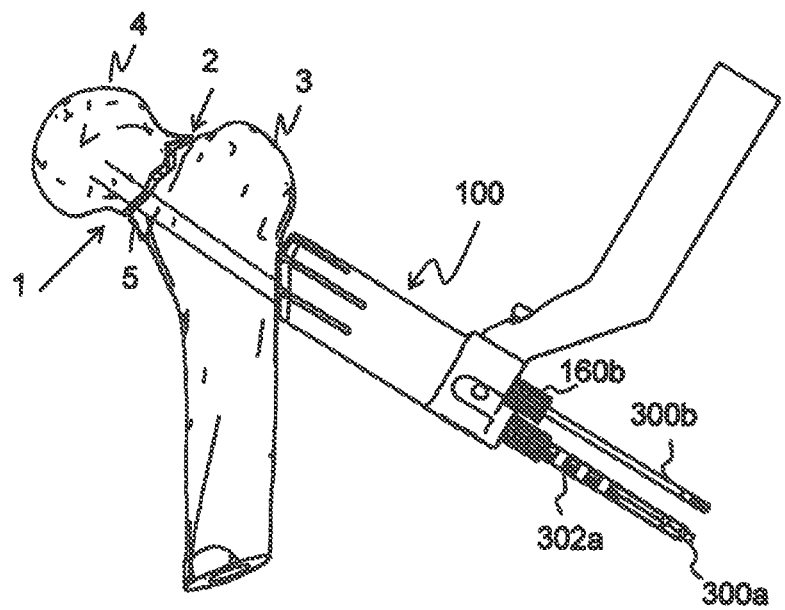
Figure 9J:
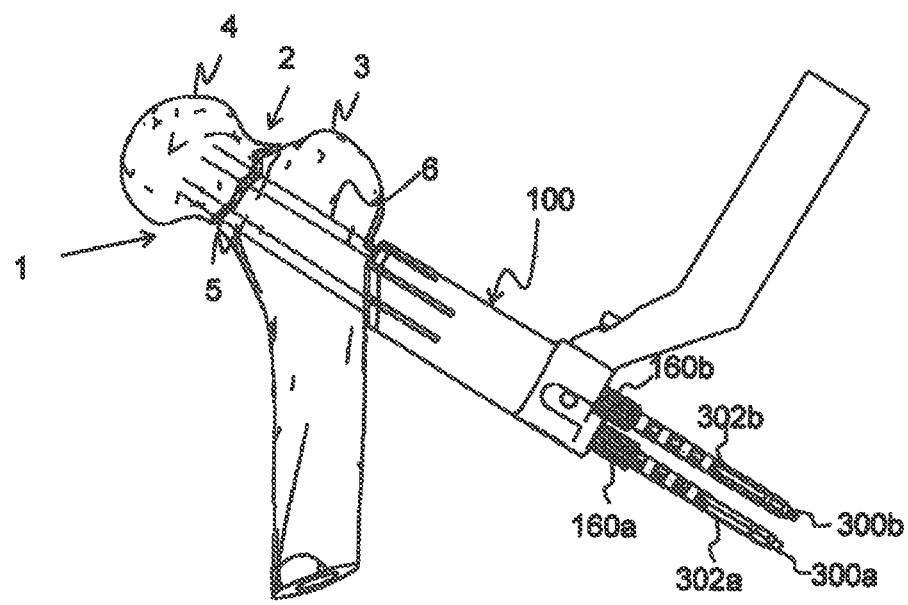
Figure 9K:
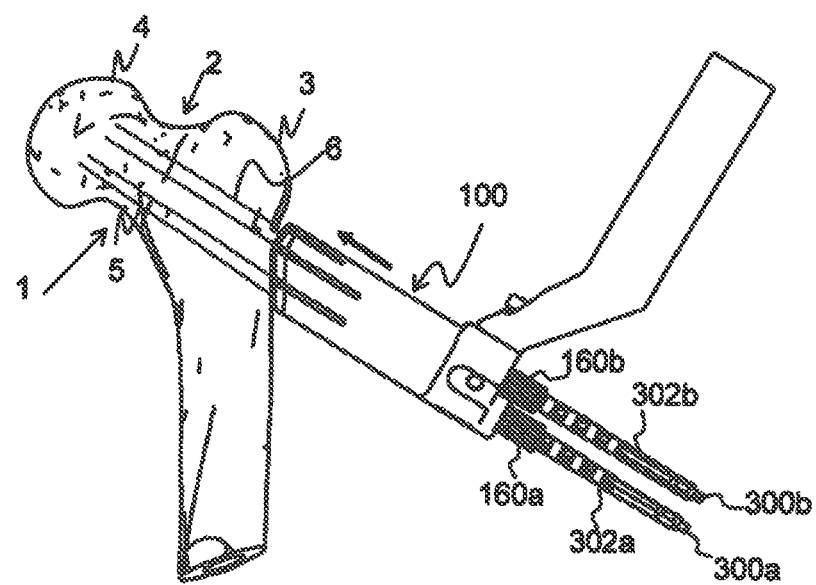
Figure 9L:
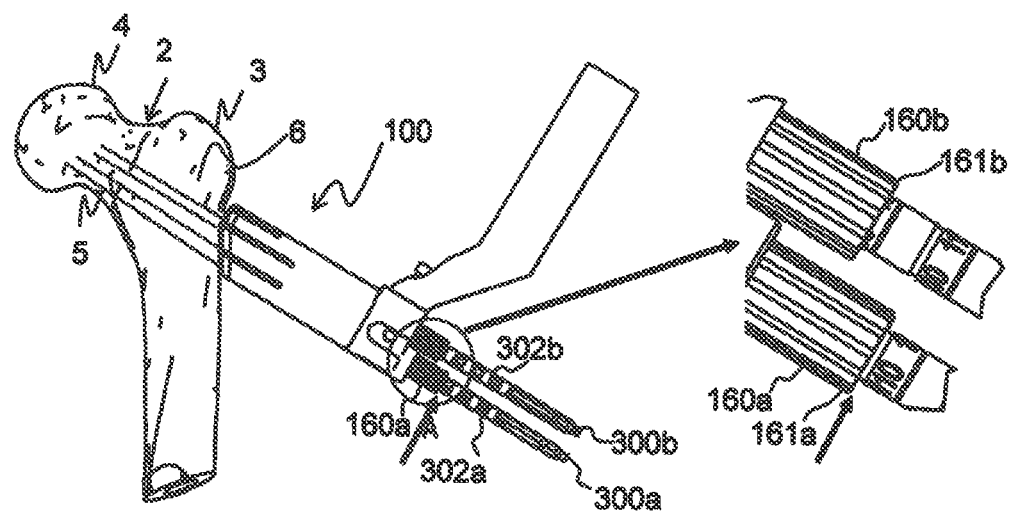
Figure 9M:
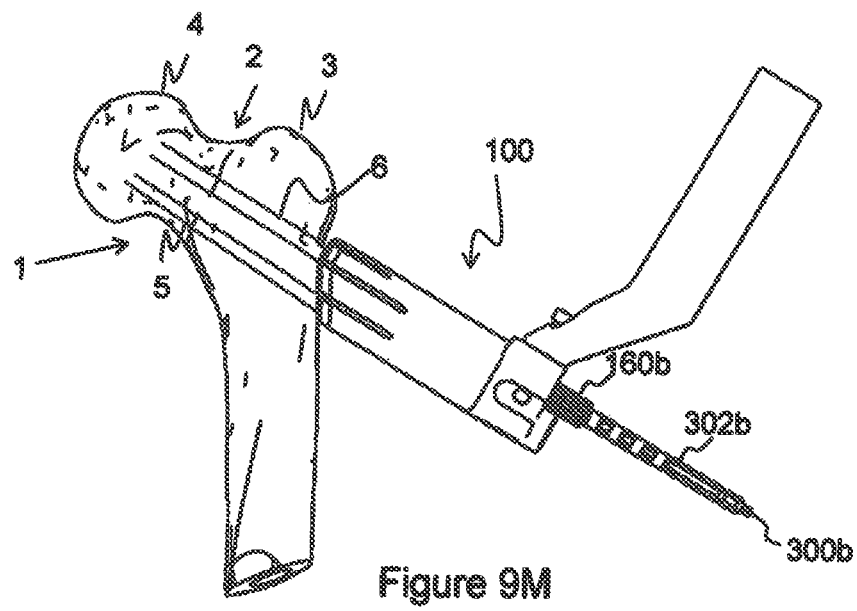
Figure 9N:
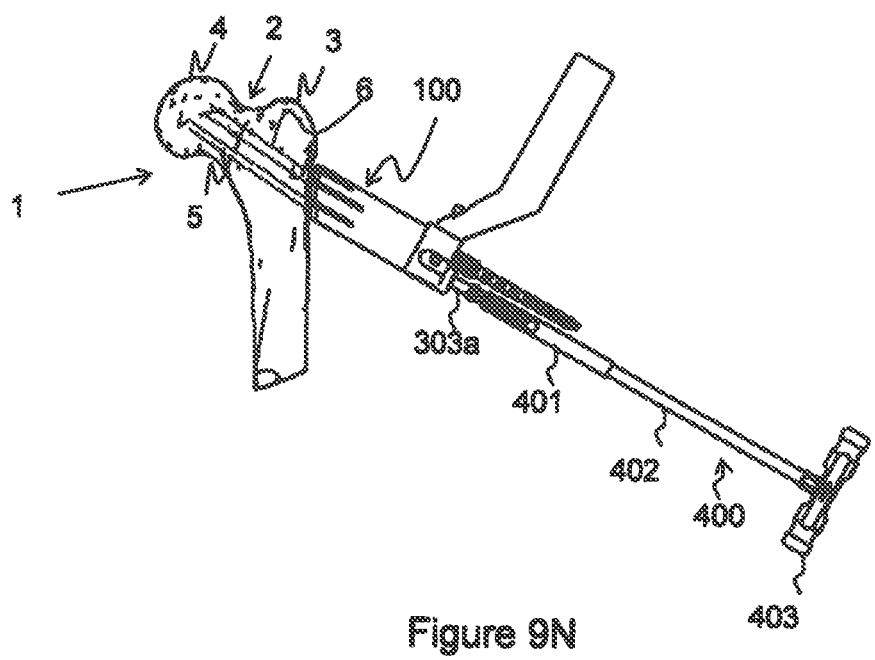
Figure 9O:
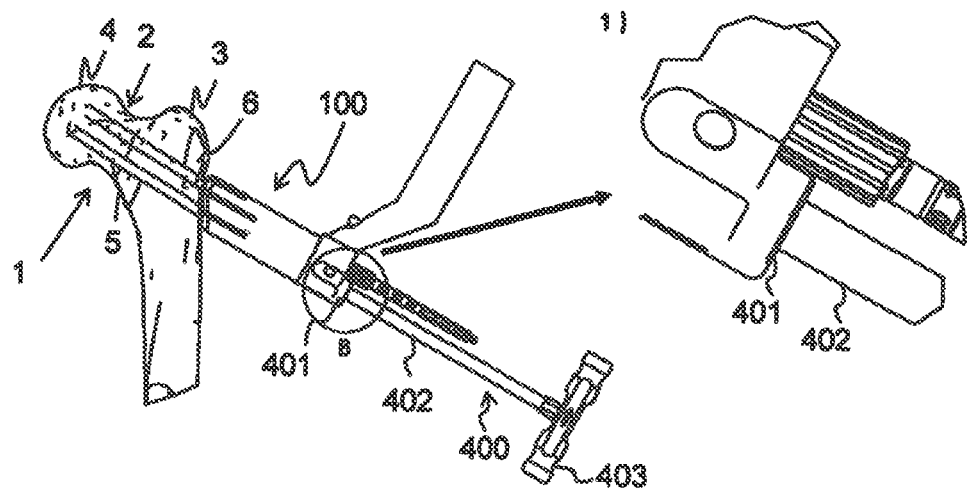
Figure 9P:
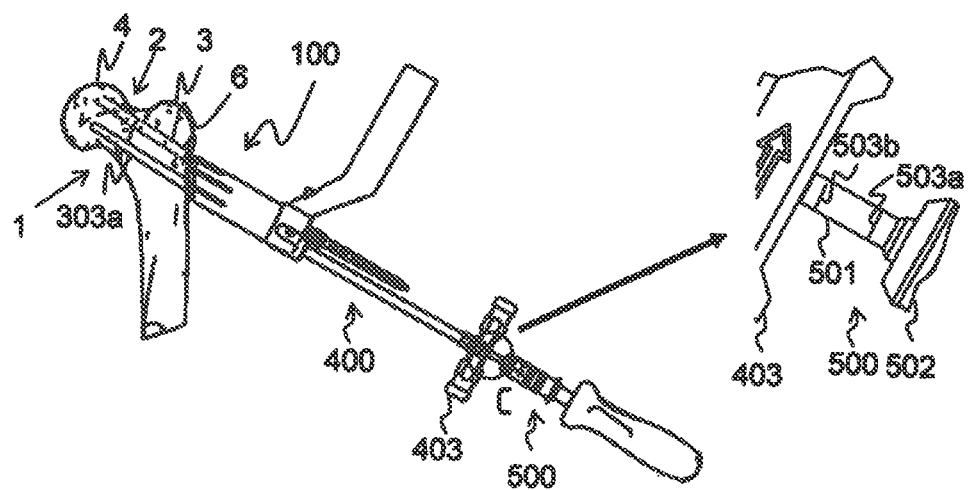
Figure 9Q:
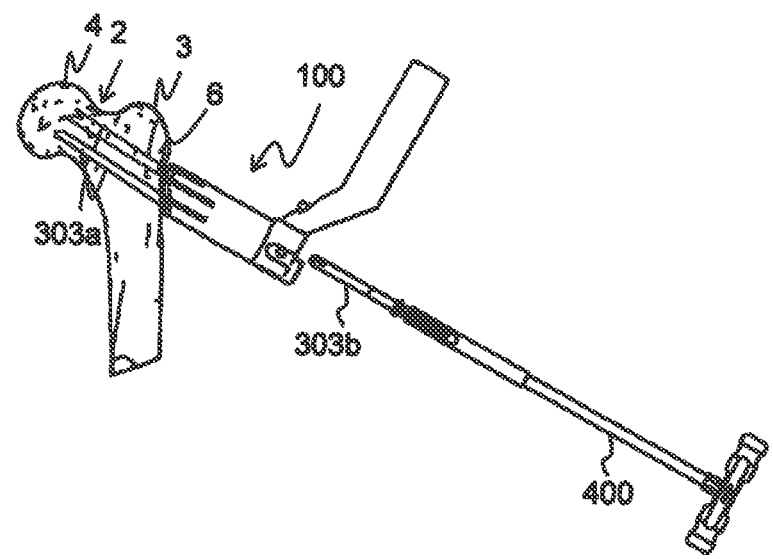
Figure 9R:
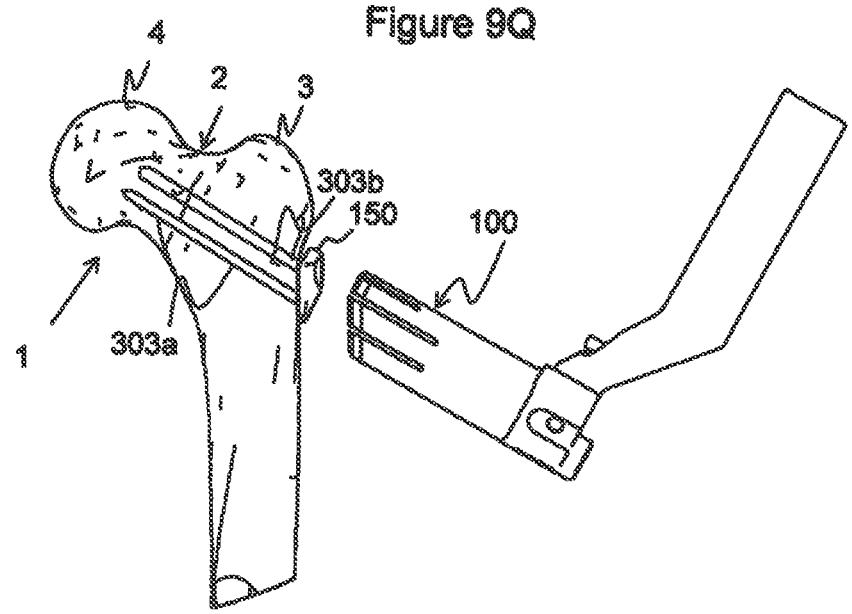
Figures 9S, 9T:
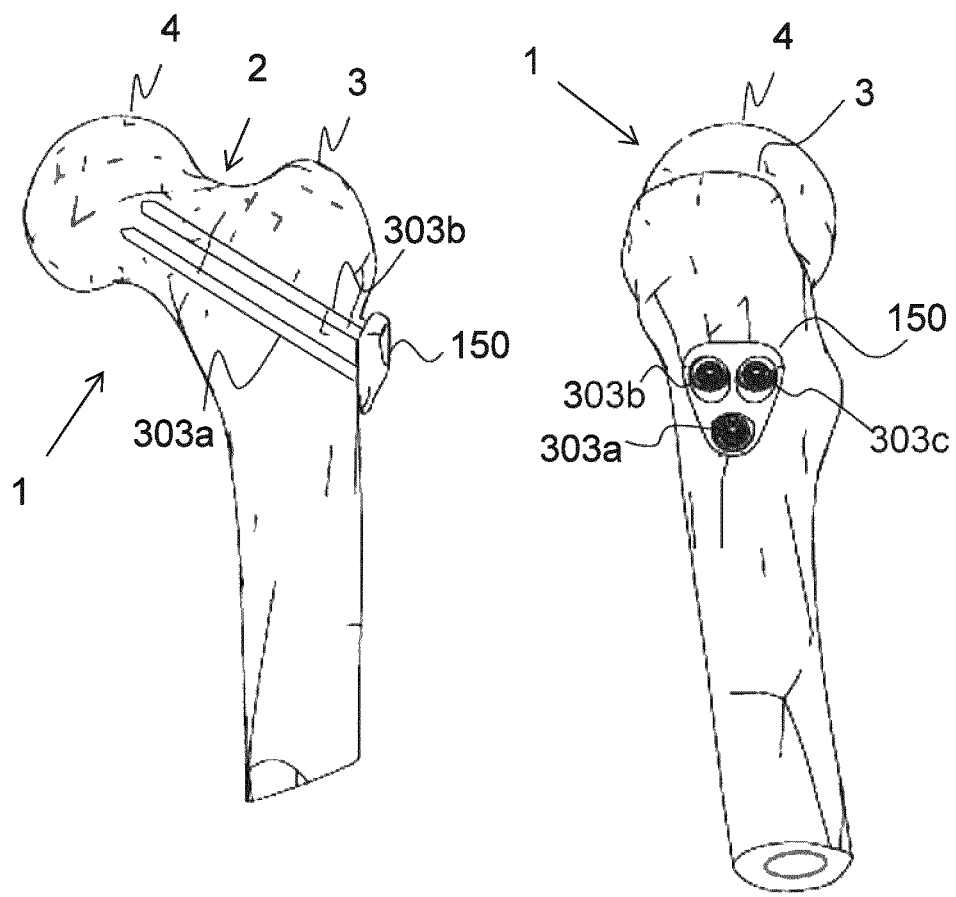

A method for fixation of bone fragments at a bone fracture using the targeting device 100 will now be described with reference to a flow chart depicted in FIG. 8 and to FIGS. 9A-9T schematically illustrating how devices described herein are arranged in relation to a femur neck when performing embodiments of the method. The method comprises one or more of the following actions. It should be understood that actions may be taken in another suitable order and that actions may be combined. Further, one or more of the actions may be optional. Furthermore, one or more of the actions may be performed during fluoroscopy or during another imaging technique.

Action 801

The method comprises exerting a distally directed traction force to the femoral neck 1 comprising the bone fracture 2. This is done in order to be able to rotate the femur and to set the bone fracture 2 in the correct anatomical position. Thereby, correct positioning of the guiding device 200 in a lateral plane and in a side plane is enabled.

Action 802

Further, the method comprises arranging the guiding device 200 in contact with an outside surface of the outer bone fragment 3 of the femoral neck 1.

This is schematically illustrated in FIG. 9A.

Action 803

By means of the guiding device 200, introducing a first guide wire 300a into a hole, e.g. a first hole 5, drilled through the outer bone fragment 3 and into the inner bone fragment 4 of the femoral neck 1. The outer and inner bone fragments 3,4 are located on opposite sides of the fracture 2.

This is schematically illustrated in FIG. 9A.

Action 804

The method comprises determining the fixation plate 150 to be used. This may be done during for example fluoroscopy and the size of the fixation plate 150 may be determined based on the position of a guide wire indicated by the aiming means 230 of the guiding device 220. The size of the fixation plate 150 may for example be given as 6, 8, 10 or 12 mm indicating the diameter of the fixation through hole 151 of the fixation plate 150. As will be described below, the fixation means 303 to be used will be selected such as the diameter of the fixation means 303 will mate the diameter of the through hole 151 of the fixation plate 150.

This is schematically illustrated in FIG. 9B.

Action 805

The method comprises removing the guiding device 200 from being in contact with the outer bone fragment 3. After removal of the guiding device 200, the first guide wire 300a remains arranged in the outer bone fragment 3 and into the inner bone fragment 4.

Action 806

A drill sleeve 301a is arranged over the first guide wire 300a. As mentioned above, the first guide wire 300a is arranged through the outer bone fragment 3 and into the inner bone fragment 4.

This is schematically illustrated in FIG. 9C.

Action 807

A cannulated drill 302a is arranged through the drill sleeve 301 and over the first guide wire 300a. Thus, the cannulated drill 302a is guided through the drill sleeve 301 and into contact with the outer bone fragment 3 by means of the first guide wire 300a.

This is schematically illustrated in FIG. 9C.

Action 808

The first drill hole 5 is drilled through the outer bone fragment 3 into the inner bone fragment 4 by advancing the cannulated drill 302a through the outer bone fragment 3 into the inner bone fragment 4. The cannulated drill 302a is advanced into the inner bone fragment 4 until a desired position is reached. The position may be a position in a subchondral bone.

This is schematically illustrated in FIG. 9C.

Action 809

The method further comprises removing the drill sleeve 301a. After removal of the drill sleeve 301a, the first guide wire 300a and the cannulated drill 302a remain arranged in the outer bone fragment 3 and into the inner bone fragment 4. Especially, the cannulated drill 302a is retained in the drilled first hole 5.

Action 810

The first, second and third drill sleeves 160; 160a,160b, 160c are attached to the fixation plate 150, e.g. to the fixation plate having the dimensions determined in Action 1104 above. FIG. 9D schematically illustrates a stand 180 comprising four sets of three pins 181, wherein the pins of each set have the same diameter such as 6, 8, 10, and 12 mm. As schematically illustrated in FIG. 9D, the fixation plate 150 having three through holes 151; 151a, 151b, 151c are arranged at the set of pins 181 having a diameter of 8 mm, and the first, second and third drill sleeves 160; 160a,160b, 160c are arranged at the respective pin 181 and at the fixation plate 150.

Action 811

The method comprises pushing the elongated body portion 110 of the targeting device 100 over the first, second and third drill sleeves 160a, 160b, 160c until the fixation plate 150 is attached to the second end 112 of the targeting device 100 by means of the snap-fitting means 114. The targeting device 100 may be selected based on the size of the fixation plate 150 determined in Action 804 above such that the snap-fitting means 114 of the selected targeting device 100 has a dimension suitable to retain the selected fixation plate 150.

FIG. 9E schematically illustrates how the elongated body portion 110 of the targeting device 100 is pushed over the first, second and third drill sleeves 160a, 160b, 160c until the fixation plate 150 is attached to the second end 112 of the targeting device 100 by means of the snap-fitting means 114. FIG. 9F schematically illustrates an assembled targeting device 100 comprising a respective guide wire sleeve 170; 170a, 170b, 170c arranged in the respective drill sleeves 160; 106a, 160b, 160c.

Action 812

Further, the method comprise arranging the targeting device 100 in contact with the outside surface of the outer bone fragment 3 of the femoral neck 1 by arranging the first drill sleeve 160a over the cannulated drill 302a and the first guide wire 301a. As previously mentioned in Action 809, the first guide wire 300a and the cannulated drill 302a are arranged in the outer bone fragment 3 and into the inner bone fragment 4.

This is schematically illustrated in FIG. 9G.

Action 813

By means of the targeting device 100, a respective second and third drill 302b, 302c are introduced in the second and third drill sleeves 160b, 160c, respectively.

In some embodiments comprising a cannulated techniques, e.g. when the second and third drills 302b, 302c are cannulated drills, the introducing of the respective second and third drill 302b, 302c in the second and third drill sleeves 160b, 160c, respectively, comprises:

- introducing a second guide wire sleeve 170b into the second drill sleeve 160b;
- introducing a third guide wire sleeve 170c into the third drill sleeve 160c;
- introducing a respective second and third guide wire 300b, 300c in the respective second and third guide wire sleeves 170b, 170c through the outer bone fragment 3 and into the inner bone fragment 4;
- removing the second and third guide wire sleeves 170b, 170c; and
- introducing the respective second and third cannulated drill 302b, 302c through the respective second and third drill sleeves 160b, 160c and over the respective second and third guide wires 170b, 170c.

The guide wire sleeves 170; 170a, 170b, 170c may have an inner diameter in the range of 3-4 mm, e.g. 3.2 mm.

This is schematically illustrated in FIGS. 9H-9J.

Action 814

Further, by means of the second and third drills 302b, 302c, a respective second and third drill hole 6,7 are drilled through the outer bone fragment 3 and into the inner bone fragment 4.

This is schematically illustrated in FIG. 9J. However, in FIG. 9J, the third drill hole 7 and the third drill 302c are arranged parallel to the second hole 6 and the second drill 302b.

Action 815

The method may further comprise releasing of the distally directed traction force exerted to the femoral neck 1. Thereby, the distance between the inner and outer bone fragments 3, 4 and the fracture 2 will be reduced.

Action 816

The targeting device 100 is pushed along its longitudinal direction towards the femoral neck 1. This is done in order to reduce the distance between the inner and outer bone fragments 3, 4 and the fracture 2 to a minimum.

This is schematically illustrated in FIG. 9K.

Action 817

The method further comprises reading off a respective length of the drilled first, second and third drill holes 5, 6, 7, at respective outer ends 161; 161a, 161b, 161c of the respective drill sleeves 160; 160a, 160b, 160c. Based on the respective read off length, a suitable length of a respective fixation means 303a, 303b, 303c may be selected.

This is schematically illustrated in FIG. 9L.

Action 818

Further, the method comprises sequentially performing a number of actions relating the fixation of one fixation means 303 to the inner bone fragment 4 and to the fixation plate 150. When one of the fixation means 303 has been fixated, the actions are repeated for the next fixation means. This is repeated until all fixation means 303 have been fixated to the inner bone fragment 4 and to the fixation plate 150.

Thus, the method comprises sequentially performing removal of the first drill 302a and of the first drill sleeve 160a from the targeting device 100. Thereafter, a first fixation means 303a having a selected length is introduced through the first body through hole 113a of the elongated body portion 110 into the first drill hole 5. Then, the first fixation means 303a is attached to the inner bone fragment 4 and to the fixation plate 150.

When the first fixation means 303a is attached to the inner bone fragment 4 and to the fixation plate 150, the second drill 302b and the second drill sleeve 160b are removed from the targeting device 100. Thereafter, a second fixation means 303b having a selected length is introduced through the second body through hole 113b of the elongated body portion 110 into the second drill hole 6. Then, the second fixation means 303b is attached to the inner bone fragment 4 and to the fixation plate 150.

The actions described above may be repeated as long as there are fixation means to be attached to the inner bone fragment 4 and to the fixation plate 150.

The fixation means 303 may be attached to the inner bone fragment 4 by deploying a hook (not shown) extending out from the fixation means 303 and into the inner bone fragment 4. The deployment of the hook may result in a pulling force exerted on the fixation plate 150. Further, the fixation means 303 may for example be attached to the fixation plate 150 by means of outer threads of the fixation means 303 mating internal threads of the respective through hole 151 of the fixation plate 150. Thus, by means of a fixation insertion means 400, the fixation means 303 may be screwed into the inner bone fragment 4 and attached at the fixation plate 150, whereby the screwing results in a pushing force being exerted on the fixation plate 150.

The fixation means 303 may have a sleeve and, disposed therein, a pin arranged for movement in the sleeve so that at least a forward portion of the pin may be driven outwards through at least one side aperture in the sleeve, in which case this forward portion constitutes a first fixing portion in the form of at least one hook, e.g. the hook mentioned above, which engages in the inner bone fragment 4. As the density in the inner bone fragment 4 is greatest at its centre, it is of advantage if the respective fixation means 303 is applied in such a way that the forward portion of the pin is caused, during the driving, to engage in the central portions of the bone fragment 4. The respective fixation means 303 may also be so configured as to achieve engagement in the central portions of the inner bone fragment. For example, when the fixation means 303 comprises a threaded second fixing portion, the threads therein may be so disposed and/or configured that said result is achieved. Having the forward portion of the pin in the respective fixation means 303 pointing towards the centre of the inner bone fragment 4 not only means that the fixation means 303 have a better grip in the inner bone fragment but also counteracts the risk of rotation or other movement of the bone nails. The first and second fixing portions of the fixation means may also be other than threaded portions.

The fixation insertion means 400 comprises a first elongated rod section 401 having a first diameter, a second elongated rod section 402 having a second diameter, and a handle portion 403. The first diameter is larger than the second diameter. The length of the first elongated rod section 401 mates the length of the through holes 113 of the targeting device 100 such that the first elongated rod section 401 fits flush with the elongated body portion 110 when the fixation means 303 has been inserted completely. The fixation insertion means 400 may be a screw driver comprising a tip that is inserted in a screw head of the fixation means 303.

A hook deployment means 500 is arranged at the second elongated rod section 402 of the fixation insertion means 400. The hook deployment means 500 comprises an elongated rod 501 and a handle means 502. The elongated rod 501 may comprise a first indication 503a configured to indicate, e.g. visualise, when the hook is completely deployed and a second indication 503b configured to indicate, e.g. visualise, when the hook is retracted.

The hook deployment means 500 may be a screw driver comprising a tip that is inserted in a screw head at the second elongated rod section.

It should be understood that when the fixation means 303 are attached to the inner bone fragment 4 and to the fixation plate 150, the fixation plate 150 is released from the targeting device's snap-fitting means 114 by means of the force exerted on the fixation plate 150.

This is schematically illustrated in FIGS. 9N-9Q.

Action 819

The targeting device 100 is removed from being in contact with the outer bone fragment 3 of the femoral neck 1.

This is schematically illustrated in FIG. 9R. Further, FIGS. 9S and 9T schematically shows two different views of the femoral neck 1 with the fixation plate 150.

A bone nail may have a sleeve and, disposed therein, a pin arranged for movement in the sleeve so that at least a forward portion of the pin can be driven outwards through at least one side aperture in the sleeve, in which case this forward portion constitutes a first fixing portion in the form of at least one hook which engages in the inner bone fragment, and the respective bone nail has in addition a second fixing portion of the type described above. As the density in the inner bone fragment is greatest at its centre, it is of advantage if the respective bone nail is applied in such a way that the forward portion of the pin is caused, during the driving, to engage in the central portions of the bone fragment. The respective bone nail may also be so configured as to achieve engagement in the central portions of the inner bone fragment. For example, where there is a threaded second fixing portion, the threads therein may be so disposed and/or configured that said result is achieved. Having the forward portion of the pin in the respective bone nail pointing towards the centre of the inner bone fragment not only means that the bone nails have a better grip in the inner bone fragment but also counteracts the risk of rotation or other movement of the bone nails. Said first and second fixing portions of the fixation means may also be other than threaded portions. The size and choice of material of the constituent items of an operating set may vary as necessary and desired.

When using the word "comprise" or "comprising" it shall be interpreted as non-limiting, i.e. meaning "consist at least of".

The embodiments herein are not limited to the above described preferred embodiments. Various alternatives, modifications and equivalents may be used. Therefore, the above embodiments should not be taken as limiting the scope of the invention, which is defined by the appending claims.

The invention claimed is:

1. A targeting device (100) configured for fixation of bone fragments (3,4) at a bone fracture (2) in a femoral neck, wherein the targeting device (100) comprises:

an elongated body portion (110) comprising a first body end (111) and an opposed second body end (112), wherein the elongated body portion (110) comprises two or more substantially parallel body through holes (113a,113b,113c) extending from the first body end (111) to the second body end (112) for guiding respective fixation means (303;303a,303b,303c) through the body portion (110), and a bracket (120) arranged at the first body end (111), wherein the body portion (110) in its second body end (112) has a snap-fitting means (114) comprising one or more slits (114a,114b,114c) distributed around an envelope surface (112a) of the second body end (112), each one of the one or more slits (114a,114b,114c) extends in a longitudinal direction that is approximately parallel with a longitudinal direction of the body portion (110), and the one or more slits (114a,114b,114c) enable the second body end (112) to flex outwards and clamp around a fixation plate (150) having a circumference that is larger than a circumference of the second body end (112) in an unflexed position, thereby enabling the second body end (112) to removably receive and attach the fixation plate (150) and drill sleeves attached to the fixation plate, from a holding arrangement, to the body portion (110) such that at least one fixation through hole (151) of the fixation plate (150) is located in line with at least one of the two or more substantially parallel body through holes (113a, 113b,113c) and, when in use, to provide a surface of the fixation plate (150) to be configured to abut a surface of an outer bone fragment (3) for subsequent fixation of the fixation plate (150) to the outer bone fragment (3) by the fixation means (303;303a,303b,303c), wherein the first body end (111) comprises a first joint portion (115) and the bracket (120) comprises a mating second joint portion (126), and wherein the first joint portion (115) and the mating second joint portion (126) are configured to removably attach the body portion (110) and the bracket (120) to each other.

2. The targeting device (100) of claim 1, wherein the second body end (112) is provided with a chamfered end section (112b) arranged in a plane angled in relation to an axial plane of the body portion (110), and wherein a surface of the chamfered end section (112b) is configured to abut a surface of the outer bone fragment (3) when in use.

3. The targeting device (100) of claim 2, wherein the chamfered end section (112b) is configured to fit flush with the fixation plate (150) when the second body end (112) in use clamps around the fixation plate (150).

4. The targeting device (100) of claim 2, wherein the snap-fitting means (114) and the fixation plate (150) are arranged such that the fixation plate (150) is angled to fit flush with the chamfered end section (112b) when attached to the targeting device (100) by means of the snap-fitting means (114).

5. The targeting device (100) of claim 1, wherein the first joint portion (115) comprises a slot (115a) configured to retain a protruding rim (126a) of the mating second joint portion (126) when the protruding rim (126a) is inserted into the slot (115a) by means of a force applied to the bracket (120) in a direction from the first body end (111) towards the second body end (112) and configured to release the protruding rim (126a) from the slot (115a) when a force is applied to the bracket (120) in a direction from the second body end (112) towards the first body end (111).

6. The targeting device (100) of claim 5, comprising a removable fastening means (124) configured to securely attach the bracket (120) at the first body end (111).

7. The targeting device (100) of claim 6, wherein the body portion (110) comprises a recess (115b) arranged at the slot (115a) and extending in a direction perpendicular to the longitudinal direction of the body portion (110), wherein the bracket (120) comprises a bracket through hole (125) extending through at least a part of the bracket (120) and wherein the removable fastening means (124) is securely arranged at the bracket (120) and extending extends through the bracket through hole (125) and into the recess (115b) of the body portion (110).

8. The targeting device (100) of claim 7, wherein the removable fastening means (124) is a screw comprising external threads (124a) at at least a part thereof and wherein the bracket through hole (125) comprises mating internal threads (125a) formed into at least a part thereof.

9. The targeting device (100) of claim 1, wherein the bracket (120) comprises a first bracket portion (121) and a second bracket portion (122), wherein the first and second bracket portions (121,122) are arranged at an angle θ relative to each other.

10. The targeting device (100) of claim 1, wherein the two or more substantially parallel body through holes (113a, 113b,113c) are each configured to encompass a respective mating one of the drill sleeves (160a,160b,160c).

11. The targeting device (100) of claim 1, wherein the number of fixation through holes (151) of the fixation plate (150) equals the number of body through holes (113a,113b, 113c) so that each fixation through hole (151) is located in line with a respective body through hole (113a,113b,113c) when the fixation plate (150) is attached to the body portion (110).

12. The targeting device (100) of claim 1, wherein when the fixation plate (150) is attached to the body portion (110), the circumference of the second body end (112) is flexed to be larger than the circumference of the fixation plate (150) and the second body end (112) clamps around an entire circumference of the fixation plate (150).

13. The targeting device (100) of claim 1, wherein a length of the body portion (110) in the longitudinal direction of the body portion (110) is greater than a length of the body portion (110) in an axial direction of the body portion (110), the axial direction of the body portion (110) being transverse to the longitudinal direction of the body portion (110), the two or more substantially parallel body through holes (113a, 113b,113c) longitudinally extending through the body portion (110).

14. The targeting device (100) of claim 13, wherein the first body end (111) includes an outer surface that faces in the axial direction, the bracket (120) being joined to the axially facing outer surface of the first body end (111).

15. A system for fixation of bone fragments at a bone fracture (2) in a femoral neck, the system comprising:
  the targeting device (100) of claim 1;
  two or more drill sleeves (160a,160b,160c) attached to the fixation plate (150), each drill sleeve (160a,160b,160c) being configured to be received in a corresponding body through hole (113a,113b,113c); and
  the holding arrangement (180) for holding the two or more drill sleeves (160a,160b,160c) prior to use of the two or more drill sleeves (160a,160b,160c).

16. A system for fixation of bone fragments at a bone fracture (2) in a femoral neck, the system comprising:
  a targeting device (100) configured for fixation of bone fragments (3,4), the targeting device (100) comprising:
    an elongated body portion (110) comprising a first body end (111) and an opposed second body end (112), wherein the elongated body portion (110) comprises two or more substantially parallel body through holes (113a,113b,113c) extending from the first body end (111) to the second body end (112) for guiding respective fixation means (303;303a,303b,303c) through the body portion (110), and
    a bracket (120) arranged at the first body end (111), wherein the body portion (110) in its second body end (112) has a snap-fitting means (114) comprising one or more slits (114a,114b,114c) distributed around an envelope surface (112a) of the second body end (112), each one of the one or more slits (114a,114b, 114c) extends in a longitudinal direction that is approximately parallel with a longitudinal direction of the body portion (110), and the one or more slits (114a,114b,114c) enable the second body end (112) to flex outwards and clamp around a fixation plate (150) having a circumference that is larger than a circumference of the second body end (112) in an unflexed position thereby enabling the second body end (112) to removably attach the fixation plate (150) to the body portion (110) such that the second body end is configured to receive corresponding drill sleeves attached to the fixation plate with a specific size and fixation through holes (151) of the fixation plate (150) are located in line with respective ones of the body through holes (113a,113b,113c) and, when in use, to provide a surface of the fixation plate (150) to be configured to abut a surface of an outer bone fragment (3) for subsequent fixation of the fixation plate (150) to the outer bone fragment (3) by the fixation means (303;303a,303b,303c), wherein the first body end (111) comprises a first joint portion (115), wherein the bracket (120) comprises a mating second joint portion (126), and wherein the first joint portion (115) and the mating second joint portion (126) are configured to removably attach the body portion (110) and the bracket (120) to each other; and
  a stand (181) comprising a number of pins corresponding to the number of body through holes of the body portion (110) for receiving an assembly comprising at least one fixation plate (150) and corresponding drill sleeves (116a, 116b, 116c), the stand being configured to, in use, cooperate with the targeting device to provide an assembly with a selected diameter.

17. The system of claim 16, further comprising a guiding device (200).

18. The system of claim 17, wherein the guiding device (200) is configured to ensure an angle α between the fixation plate (150) and one of the fixation means (303), and comprises an elongated guide portion (211) comprising, in its longitudinal direction, a longitudinal through hole (212) configured to guide a guide wire through the guide portion (211) from an inlet opening (213) in a first end (214) of the guide portion (211) to an outlet opening (215) in a second end (216) of the guide portion (212).

19. A method for fixation of bone fragments at a bone fracture, wherein the method comprises:
  providing the targeting device of claim 1;
  exerting (801) a distally directed traction force to a femoral neck (1) comprising a bone fracture (2);
  arranging (802) a guiding device (200) in contact with an outside of an outer bone fragment (3) of the femoral neck (1);
  by means of the guiding device (200), introducing (803) a first guide wire (300a) into a hole drilled through the outer bone fragment (3) and into an inner bone fragment (4) of the femoral neck (1);
  determining (804) a fixation plate (150) to be used;
  removing (805) the guiding device (200) from being in contact with the outer bone fragment (3);
  arranging (806) a drill sleeve (301) over the first guide wire (300a) arranged through the outer bone fragment (3) and into the inner bone fragment (4);
  arranging (807) a first cannulated drill (302a) through the drill sleeve (301) and over the first guide wire (300);
  drilling (808) a first hole (5) through the outer bone fragment (3) into the inner bone fragment (4) by advancing the first cannulated drill (302*a*) through the outer bone fragment (3) into the inner bone fragment (4);

removing (809) the drill sleeve (301);

attaching (810) first, second and third drill sleeves (160; 160*a*,160*b*,160*c*) to the fixation plate (150);

pushing (811) the elongated body portion (110) of the targeting device (100) over the first, second and third drill sleeves (160*a*,160*b*,160*c*) until the fixation plate (150) is attached to the second end (112) of the targeting device (100) by means of the snap-fitting means (114);

arranging (812) the targeting device (100) in contact with the outside of the outer bone fragment (3) of the femoral neck (1) by arranging the first drill sleeve (160*a*) over the first cannulated drill (302*a*) and the first guide wire (301*a*);

by means of the targeting device (100), introducing (813) a respective second and third drill (302*b*,302*c*) in the second and third drill sleeves (160*b*,160*c*), respectively;

by means of the second and third drills (302*b*,302*c*), drilling (814) a respective second and third drill hole (6,7) through the outer bone fragment (3) into the inner bone fragment (4);

releasing (815) the distally directed traction force exerted to the femoral neck (1);

pushing (816) the targeting device (100) along its longitudinal direction towards the femoral neck (1);

reading (817) off a respective length of the drilled first, second and third holes (5,6,7), at respective outer ends (161;161*a*,161*b*,161*c*) of the respective drill sleeves (160*a*,160*b*,160*c*);

sequentially performing (818), removal of the respective first, second and third drills (302*a*, 302*b*,302*c*) and the respective first, second and third drill sleeves (160*a*, 160*b*,160*c*) from the targeting device (100), introduction of a respective first, second and third fixation means (303;303*a*,303*b*,303*c*) having a respective selected length through respective first, second and third body through holes (113*a*,113*b*,113*c*) of the elongated body portion (110) into the respective first, second and third drill holes (5,6,7) and attachment of the respective first, second and third fixation means (303; 303*a*,303*b*,303*c*) to the inner bone fragment (4) and to the fixation plate (150); and removing (819) the targeting device (100) from being in contact with the outer bone fragment (3) of the femoral neck (1).

20. The method of claim 19, wherein the second and third drills (302*b*,302*c*) are cannulated drills, and wherein the introducing (813) of the respective second and third drill (302*b*,302*c*) in the second and third drill sleeves (160*b*, 160*c*), respectively, comprises:

introducing a second guide wire sleeve (170*b*) into the second drill sleeve (160*b*);

introducing a third guide wire sleeve (170*c*) into the third drill sleeve (160*c*);

introducing a respective second and third guide wire (300*b*,300*c*) in the respective second and third guide wire sleeves (170*b*,170*c*) through the outer bone fragment (3) and into the inner bone fragment (4);

removing the second and third guide wire sleeves (170*b*, 170*c*); and introducing the respective second and third cannulated drills (302*b*,302*c*) through the respective second and third drill sleeves (160*b*,160*c*) and over the respective second and third guide wires (170*b*,170*c*).

* * * * *